US009259458B2

(12) United States Patent
Favre et al.

(10) Patent No.: US 9,259,458 B2
(45) Date of Patent: *Feb. 16, 2016

(54) THERAPEUTIC USE OF AT LEAST ONE BOTULINUM NEUROTOXIN IN THE TREATMENT OF PAIN ASSOCIATED WITH DIABETIC NEUROPATHY

(71) Applicant: IPSEN PHARMA S.A.S., Boulogne-Billancourt (FR)

(72) Inventors: Christine Favre, Saint Maurice Montcouronne (FR); Michel Auguet, Palaiseau (FR); Piere-Etienne Chabrier De Lassauniere, Paris (FR)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/174,911

(22) Filed: Feb. 7, 2014

(65) Prior Publication Data

US 2014/0154781 A1 Jun. 5, 2014

Related U.S. Application Data

(63) Continuation of application No. 12/989,608, filed as application No. PCT/IB2009/005750 on Apr. 27, 2009, now Pat. No. 8,784,841.

(30) Foreign Application Priority Data

Apr. 25, 2008 (FR) ...................................... 08 02321

(51) Int. Cl.
*A61K 38/48* (2006.01)
*A61K 38/16* (2006.01)

(52) U.S. Cl.
CPC ............. *A61K 38/4893* (2013.01); *A61K 38/16* (2013.01)

(58) Field of Classification Search
None
See application file for complete search history.

(56) References Cited

U.S. PATENT DOCUMENTS

| 4,457,916 | A | 7/1984 | Hayashi et al. | |
|---|---|---|---|---|
| 6,368,605 | B1 | 4/2002 | Donovan | |
| 7,704,524 | B2 | 4/2010 | Donovan | |
| 8,273,359 | B2 | 9/2012 | Favre et al. | |
| 8,778,904 | B2* | 7/2014 | Feinstein et al. | 514/44 A |
| 8,784,841 | B2* | 7/2014 | Favre et al. | 424/247.1 |
| 8,895,536 | B2* | 11/2014 | Bannister et al. | 514/159 |
| 8,921,322 | B2* | 12/2014 | Favre | A61K 38/4893 424/184.1 |
| 9,006,274 | B2* | 4/2015 | Chabrier De Lassauniere | A61K 31/426 514/365 |
| 9,080,220 | B2* | 7/2015 | Auguet | A61K 38/4893 |

| 2002/0064536 | A1 | 5/2002 | Hunt | |
|---|---|---|---|---|
| 2002/0192239 | A1 | 12/2002 | Borodic et al. | |
| 2003/0138437 | A1 | 7/2003 | Hunt | |
| 2004/0247623 | A1 | 12/2004 | Cady | |
| 2005/0147625 | A1 | 7/2005 | First | |
| 2005/0152905 | A1 | 7/2005 | Omoigui | |
| 2006/0178354 | A1 | 8/2006 | Lucas | |
| 2006/0240043 | A1 | 10/2006 | Meyerson et al. | |
| 2006/0269575 | A1 | 11/2006 | Hunt | |
| 2008/0232851 | A1 | 9/2008 | Park et al. | |
| 2009/0028908 | A1 | 1/2009 | Donovan | |
| 2009/0214466 | A1 | 8/2009 | Levin | |
| 2009/0232849 | A1 | 9/2009 | Gallex et al. | |
| 2009/0232851 | A1 | 9/2009 | Auguet et al. | |
| 2010/0029566 | A1 | 2/2010 | Favre et al. | |
| 2010/0068231 | A1 | 3/2010 | Favre et al. | |
| 2011/0038893 | A1 | 2/2011 | Favre et al. | |
| 2011/0152198 | A1 | 6/2011 | Hunt | |
| 2014/0154781 | A1* | 6/2014 | Favre et al. | 435/220 |

FOREIGN PATENT DOCUMENTS

| AU | 2007259122 | 11/2012 |
|---|---|---|
| CA | 2 586 181 | 5/2006 |
| GB | 2419526 | 3/2005 |
| GB | 2419526 | 5/2005 |
| GB | 2 416 692 | 2/2006 |
| GB | 2 419 526 | 3/2006 |
| KR | 2003018827 | 3/2003 |
| WO | WO 95/17904 | 7/1995 |
| WO | WO 01/26736 | 4/2001 |
| WO | WO 01/47512 | 7/2001 |
| WO | WO 01/58472 | 8/2001 |
| WO | WO 01/76576 | 10/2001 |
| WO | WO 01/78760 | 10/2001 |
| WO | WO 2004/006954 | 1/2004 |
| WO | WO 2004/075832 | 9/2004 |
| WO | WO 2005/082339 | 9/2005 |
| WO | WO 2006/005910 | 1/2006 |
| WO | WO 2006/005912 | 1/2006 |
| WO | WO 2006/042249 | 4/2006 |
| WO | WO 2006/049248 | 5/2006 |
| WO | WO 2007/144493 | 12/2007 |

OTHER PUBLICATIONS

Restivo et al, Diabetes Care 29:2650-2653, 2006.*
Bach-Rojecky et al, European Journal of Pharmacology 633 (2010) 10-14.*
Jabbari et al, Pain Medicine 2011; 12: 1594-1606.*
Pavone et al, Toxins 2010, 2, 2890-2913.*
Ansiaux et al., Expert Opinion on Investigational Drugs. vol. 16, No. 2, pp. 209-218, XP002506486 (2007).
Aoki, NeuroToxicology, vol. 26, No. 5, pp. 785-793, XP005106270 (2005).
Argoff (2002) *The Clinical Journal of Pain* 18: S177-S181.

(Continued)

*Primary Examiner* — Nita M Minnifield
(74) *Attorney, Agent, or Firm* — Hunton & Williams LLP

(57) ABSTRACT

The present invention relates to at least one botulinum neurotoxin for treatment or prevention of pain associated with diabetic neuropathy wherein said botulinum neurotoxin is prepared for local administration, wherein the local administration is not in the central nervous system (CNS), and wherein pain is treated at a site distant to the site of administration.

14 Claims, 2 Drawing Sheets

(56) References Cited

OTHER PUBLICATIONS

Argoff, The Clinical Journal of Pain, vol. 18, pp. S177-S181, XP009093855 (2002).
Attal et al., Neurology, vol. 70, No. 11, p. A167, XP008099219 (2008).
Auguet et al., Toxicon, vol. 51, No. Suppl. 1, p. 9, XP002506488 (2008).
Bach-Rojecky et al., Journal of Neural Transmission, vol. 112, No. 2, pp. 215-219, XP002506484 (2005).
Bach-Rojecky, et al. (2005) *Croatian Med J* 46(2):201-208.
Barwood, et al. (2000) *Developmental Medicine & Child Neurology* 42: 116-121.
Blersch et al., Journal of the Neurological Sciences, vol. 205m No. 1, pp. 59-63, XP008112569 (2002).
Bueschen (1990) *Clinical Methods: The History, Physical, and Laboratory Examinations* [$3^{rd}$ Ed.] Chapter 182 "Flank Pain".
Calabrese & Resztak (1998) *Expert Opinion on Investigational Drugs* 7(12): 2043-2060.
Cata, P. et al. (2008) Brain Research (final), National Institutes of Health. 1229: 100-110.
Cui et al., Pain, vol. 107, pp. 125-133, XP002547447 (2004).
Database WPI Online, Derwent Publications Ltd., London, GB, DW: 200377, Database Accession No. AN 2003-826007 & KR-A-2003018827 (SEO K I) Mar. 6, 2003.
Dieleman et al. (2002) Archives of Internal Medicine. 162(13): 1492-1501.
Dougherty, et al. (2004) "Taxol-induced sensory disturbance is characterized by preferential impairment of myelinated fiber functions in cancer patients." *Pain* 109:132-142.
Dougherty, et al. (2004) *Pain* 109:132-142.
Farve-Guilmard, C. et al. (2009) European Journal of Pharmacology. 617: 48-53.
Favre-Guilmard et al., Toxicon, vol. 51, No. Supp. 1, p. 10, XP002506487 (2008).
Frich et al. (2000) Journal of Pain and Symptom Management. 19(5): 339-347.
Gonzalez-Duarte, et al. (2006) *The PRN Notebook* 11(2): 24-29.
Gordon, D. (Dec. 2004) Pain Management Nursing, W.B. Saunders. 5: 19-33.
Guokai et al. (2003) Chinese Journal of Anesthesiology. 23(2): 157-159.
International Search Report for International Application No. PCT/IB2009/005750 mailed Jul. 10, 2009.
International Search Report for International Application No. PCT/FR2007/000956, mailed on Feb. 22, 2008.
International Search Report for International Application No. PCT/FR2007/002091, mailed Jul. 29, 2008.
International Search Report for International Application No. PCT/FR2007/001773, mailed Apr. 28, 2008.
Jabbari et al., Pain Medicine, vol. 4, No. 2, pp. 206-210, XP002547450 (2003).
Jacobson et al., Applied and Environmental Microbiology, vol. 74, No. 9, pp. 2778-2786 (2008).
Joseph et al. (2004) Pain. 107: 147-158.
Kern, et al. (2004) *J Rehabil Med* 36: 238-239.
Kern, U., et al. (Apr. 2004) Nervenarzt. 75(4).
Keswani et al. (2002) AIDS. 16: 2105-2117.
Klein (2004) *Dermatol Surg* 30: 452-455.
Klein et al. (2004) Dermatologic Surgery 30(3): 452-455.
Klein, et al. (2004) *Dematol. Surg.* 30: 452-455.
Ledeboer, A. et al. (2007) Brain, Behavior and Immunity, Available online at www.sciencedirect.com. 21: 686-698.
Liu et al. (2006) Pain Medicine. 7(1): 89-91.
Lo Nigro et al., Medical and Pediatric Oncology, vol. 38, No. 2, p. 150, XP002506585 (2002).
Luciano et al. (2003) Current Opinion in Neurology. 16: 403-409.
Luvisetto, S. et al. (2007) NeuroScience. 145: 1-4.
Luvisetto, S. et al., Brain Research—Research Report, Available online at www.sciencedirect.com, Accepted Jan. 28, 2006.
Meyer (2008) *SA Fam Pract* 50(3): 40-49.
National Diabetes Information Clearinghouse, Diabetic Neuropathies: The Nerve Damage of Diabetes (2011).
NINDS Diabetic Neuropathy Information Page (2011).
NINDS Peripheral Neuropathy Fact Sheet (2011).
NINDS Peripheral Neuropathy Information Page (2011).
Noguera et al. (2004) AIDS. 18(2): 352-353.
Park & Moon (2008) "Antinociceptive Effects of Botulinum Toxin A for the Treatment of Neuropathic Pain." *Reviews in Analgesia* 10(1): 1-9 [Abstract only].
Park et al., Biosciences Information Service, Database Accession No. PREV200800185978, XP002506490 (2008).
Park, H.J. et al. (2006) Canadian Journal of Anesthesia. 53(5): 470-477.
Polomano, R. et al. (2001) Pain. 94: 293-304.
Ranoux et al., Annals of Neurology, vol. 64, No. 3, pp. 274-283, XP002506489 (2008).
Sudaraj, et al. (2004) *Pain Practice* 4(3): 229-234.
The Merck Index: An Encyclopedia of Chemicals and Drugs, 9th Ed., Merck & Co. (1976) p. 814.
Voller et al., Neurology, vol. 61, No. 7, pp. 940-944, XP002547449 (2003).
Webb, et al. (2006) *Drug Metab Rev.* 38(1-2): 89-116.
Yuan et al., Neurology, vol. 72, No. 17, pp. 1473-1478 (2009).

\* cited by examiner

Figure 3 :

```
D-1   D0   D2      D7   D8         D13   D14        D17    D20   D21      D23
 ↑    ↑    ↑        ↑    ↑          ↑     ↑          ↑      ↑     ↑        ↑
Weight STZ Weight Weight RS       Weight  RS       Weight Weight Blood   Weight
Blood     Blood  Blood            Blood  +Dysport   RS     RS   sugar    RS
sugar     sugar  sugar            sugar                         level
level     level  level            level             D3 after D6          D9
RS                                                  Dysport
```

THERAPEUTIC USE OF AT LEAST ONE BOTULINUM NEUROTOXIN IN THE TREATMENT OF PAIN ASSOCIATED WITH DIABETIC NEUROPATHY

CROSS-REFERENCE TO RELATED APPLICATIONS

This patent application is continuation of U.S. patent application Ser. No. 12/989,608, filed Oct. 25, 2010, which is a national stage application of International Patent Application No. PCT/IB2009/005750, filed Apr. 27, 2009, and claims priority to FR 0802321, filed Apr. 25, 2008, the disclosures of each of which are herein incorporated by reference.

FIELD OF THE INVENTION

The present invention relates to at least one botulinum neurotoxin for treatment or prevention of pain caused by or associated with peripheral neuropathy, such as diabetic neuropathy. More specifically, said at least one botulinum neurotoxin is prepared or formulated for local administration and has a distant analgesic effect.

The present invention further relates to the uses and methods of treatment of at least one botulinum neurotoxin for the treatment or prevention of pain caused by or associated with peripheral neuropathy, such as diabetic neuropathy, wherein said at least one botulinum neurotoxin is administered locally and has a distant analgesic effect upon local administration.

BACKGROUND OF THE INVENTION

Peripheral neuropathy is the dysfunction of one or more peripheral nerves (the part of a spinal nerve distal to the root and plexus). It includes numerous syndromes characterized by varying degrees of sensory disturbances, pain, muscle weakness and atrophy, diminished deep tendon reflexes, and vasomotor symptoms, alone or in any combination. Electromyography and nerve conduction velocity studies help localize the lesion and determine whether the pathophysiology is primarily axonal (often metabolic) or demyelinating (often autoimmune).

Peripheral neuropathy associated with diabetes (diabetic neuropathy) is a polyneuritis linked to the duration poor control of the underlying diabetes. It can affect the upper and lower limbs and the cranial nerves.

Diabetic neuropathy is the consequence of an impairment of certain nerves caused by diabetes. These nerves can be located anywhere in the organism, with some areas being more "at risk" than others. Depending on the type of nerves affected and the place where they are located in the organism, generally three kinds of diabetic neuropathy are distinguished.

The most frequent form is distal symmetrical polyneuropathy. This disease involves an impairment of several nerves (poly means several in Greek) in the two lower limbs (symmetrical) and is generally especially manifest in the feet (distal).

Diabetic pain is generalized and does not affect only one single organ unlike certain other types of pain, which are localized.

Known treatments of pain associated with peripheral, in particular diabetic neuropathies, include topical agents, tricyclic antidepressants, anticonvulsants, and nonoploid analgesics.

Botulinum toxin, in particular botulinum toxin type A1 (Dysport® marketed by ipsen or Botox® marketed by Allergen), has been used for human therapy since the 1980s. The diseases/disorders treated with botulinum toxin include e.g. muscle disorders (for example blepharospasm, spasticity in adults or children or torticollis), migraine, pain of muscular origin, hyperhidrosis (excessive perspiration), hypersalivation. In cosmetic applications, botulinum toxin is used to treat wrinkles.

WO 01/26736 discloses a method of treating pain associated with diabetes by intrathecal (intraspinal) administration of botulinum neurotoxin type A. This document teaches that the injected neurotoxin does not diffuse or is transported away from the CNS injection site.

US 2002/0192239 describes treatment of neuralgia-related chronic severe pain or post-operative incisional wound pain by injecting botulinum toxin into an afflicted area of a patient.

US 2004/0247623 describes the transdermal administration of botulinum toxin type A for treatment of migraine or other disorders associated with the release of certain neurotransmitters from sensory neurons. One such disease can be diabetic neuropathy. US 2004/0247623 teaches to apply the botulinum toxin directly into the affected area.

Bach-Rojecky et al. (Journal of Neural Transmission 2005, vol. 112, no. 2, p. 215-219) disclose the reduction of thermal and mechanical hyperalgesia by botulinum toxin type A in an experimental model of neuropathic pain caused by surgical neuropathy.

Argoff (Clinical Journal of Pain 2002, New York, vol. 18, no. 6, p. s177-s181) describes a study using botulinum toxin type A injections into the site of maximal pain in patients suffering from CRPS type I (Complex Regional Pain Syndrome). The patients experienced relief of their burning and dysesthetic pain in the affected extremities.

Attal et al. (Neurology 2008, vol. 70, no. 11, Suppl. 1, page A167) disclose an analgesic effect of botulinum toxin type A in patients with focal painful neuropathies upon injection into the painful area.

Lo Nigro et al. (Medical and Pediatric Oncology 2002, vol. 38, no. 2, page 150) describe a 2-year old child suffering from leukaemia and chemotherapy induced peripheral neuropathy. The child also suffered from congenital spastic contractures of the right leg, which were treated by local administration of botulinum toxin into the spastic muscle every 3 months until relaxation became manifest.

Ansiaux et al. (Expert Opinion on Investigational Drugs 2007, vol. 16, no. 2, pages 209-218) report the use of botulinum toxins in cancer therapy, in particular an effect of botulinum toxins to inhibit neurogenic contractions of tumor vessels in order to potentiate cytotoxic therapy.

An analgesic effect of botulinum toxin at a site which is distant from a local injection site for treatment of pain associated with diabetic neuropathy has not been described in the prior art.

SUMMARY OF THE INVENTION

The invention relates to at least one botulinum neurotoxin for treatment of pain associated with or caused by diabetic neuropathy, wherein said botulinum neurotoxin is prepared for local administration, wherein the local administration is not in the central nervous system (CNS), and wherein pain is treated a site distant to the site of administration.

The invention further relates to the use of at least one botulinum neurotoxin for treatment of pain associated with or caused by a peripheral neuropathy caused by diabetes (diabetic neuropathy), wherein said botulinum neurotoxin is prepared for local administration, wherein the local administration is not in the central nervous system (CNS), and wherein pain is treated at a site distant to the site of administration.

The invention further relates to a method of treating pain associated with a peripheral neuropathy associated with or caused by diabetes (diabetic neuropathy) comprising locally administering to a patient in need thereof a therapeutically effective amount of at least one botulinum neurotoxin into a site which is not the central nervous system (CNS), thereby treating said pain at a site distant to the site of administration.

In an embodiment, said diabetic neuropathy is diabetic neuropathy of an upper or lower limb.

In a further embodiment, said botulinum neurotoxin is prepared for local administration, or is locally administered, into a limb. Preferably, said botulinum neurotoxin is prepared for administration, or administered, into a hand or foot. More preferably, said botulinum neurotoxin is prepared for administration, or is administered, into the palm of a hand or the sole of a foot.

In an embodiment, said botulinum neurotoxin is prepared for local administration, or is locally administered, into one side of the body.

More preferably, the botulinum neurotoxin according to any one of the preceding claims, is prepared for administration, or is administered, into a site that is distant from a painful site.

Said botulinum neurotoxin is preferably prepared for administration, or is administered, no more frequently than once per month or no more frequently than once every six weeks or no more frequently than once every 8 weeks.

Said botulinum neurotoxin is preferably prepared for local administration, or is administered, by way of sub-cutaneous, intra-muscular or intradermal route.

In embodiments, said botulinum neurotoxin is selected from botulinum neurotoxin types A, A1, A2, A3, A4, B, C, C1, D, E, F or G.

In further embodiments, said botulinum neurotoxin is prepared for administration, or is administered, at a dose comprised between 1 U and 1500 U, more preferably between 100 and 500 U.

BRIEF DESCRIPTION OF THE FIGURES

FIG. 3 shows the injection protocol applied in the experiment leading to the results shown in FIGS. 1 and 2.

DETAILED DESCRIPTION OF THE INVENTION

Figure 1:
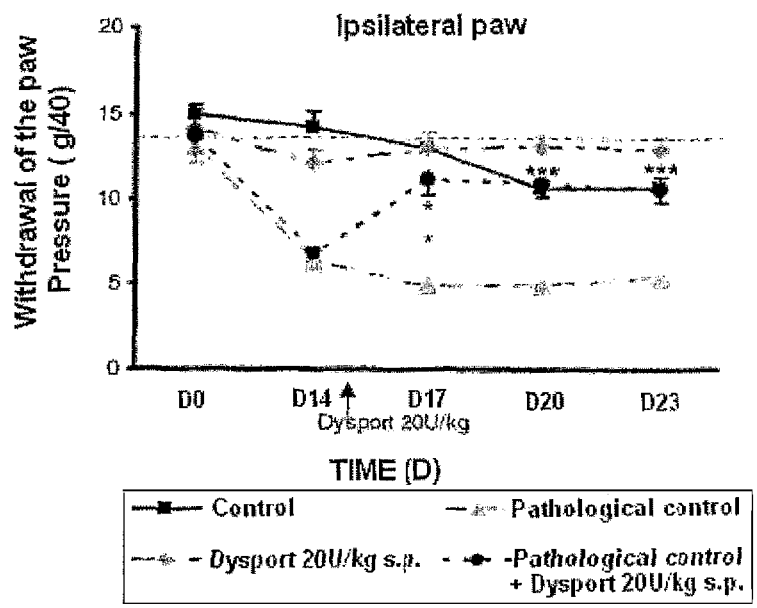
FIG. 1 shows the effect of botulinum toxin type A1 on the right paw following injection by sub-plantar route into the right paw (ipsilateral) in the model of diabetic neuropathy induced by streptozotocin described in Example 1.

The present invention is based on the observation of an analgesic effect of botulinum toxin in an in vivo animal model of diabetic neuropathy. Upon local administration of botulinum toxin into the right paw of an animal, in which diabetic neuropathy had been induced experimentally, the analgesic effect was surprisingly also observed in the left paw (i.e. on the contra-lateral side, as referring to the administration site).

Therefore, in a first aspect, the invention relates to at least one botulinum neurotoxin for treatment of pain associated with diabetic neuropathy, wherein said botulinum neurotoxin is prepared for local administration, wherein the local administration is not in the central nervous system (CNS), and wherein pain is treated at a site distant to the site of administration.

In a second aspect, the invention relates to the use of at least one botulinum neurotoxin for treatment of pain associated with diabetic neuropathy, wherein said botulinum neurotoxin is prepared for local administration, wherein the local administration is not in the central nervous system (CNS), and wherein pain is treated at a site distant to the site of administration.

In a third aspect, the invention relates to a method of treating pain associated with diabetic neuropathy comprising locally administering to a patient in need thereof a therapeutically effective amount of at least one botulinum neurotoxin into a site which is not the central nervous system (CNS), thereby treating said pain at a site distant to the site of administration.

In accordance with the present invention, local administration of a botulinum neurotoxin in a patient suffering from diabetic neuropathy leads to an analgesic effect at a remote painful site or area, i.e. an afflicted site or area which is distant from the injection site.

In the context of the present invention, the term "pain" refers to any disagreeable emotional and sensory experience associated with present or potential nerve or tissue damage, or described by the patient in such terms.

Pain associated with peripheral neuropathies such as diabetic neuropathy is e.g. described as being electric, burning, icy cold, frostbite, aching, tingling, or like "needles and pins". A delayed onset of pain can also be observed in the context of peripheral neuropathies.

An "analgesic effect", as used herein, refers to any alleviation, improvement, attenuation, reduction or decrease of pain, e.g. as experienced or evaluated by the patient.

In accordance with the present invention, the term "diabetic neuropathy" refers to any peripheral neuropathy caused by or associated with diabetes. The term includes e.g. polyneuropathies or mononeuropathies associated with diabetes. Any neuropathy caused by or associated with diabetes can be treated in accordance with the present invention, irrespective of the cause of the underlying diabetes.

Preferably, diabetic neuropathy is diabetic neuropathy of an upper limb or diabetic neuropathy of a lower limb. The neuropathy can e.g. be asymmetrical, i.e. only one side of the body can be afflicted, or only one limb. The neuropathy can also afflict both sides of the body, such as e.g. both lower limbs. An embodiment is distal symmetrical polyneuropathy.

In an embodiment, the botulinum neurotoxin is prepared for local administration into a limb.

In a further embodiment, the botulinum neurotoxin is prepared for local administration into a hand or a foot.

In accordance with the present invention, it is further preferred to prepare the botulinum toxin for administration into the palm of a hand or the sole of a foot.

In a further embodiment, local administration of botulinum neurotoxin is limited to one side of the body. In accordance with the present invention, analgesic effect is achieved on the other side of the body as well. Such an analgesic effect on the contralateral (in relation to the local administration site) side of the body is an example for treatment of pain at a site distant to the site of administration. Examples for administration sites on one side of the body are e.g. administration into the left hand, the left foot, the right hand or the right foot.

In accordance with the present invention, the botulinum neurotoxin is preferably administered no more frequently than once per month or nor more frequently than once every six weeks or no more frequently than once every 8 weeks or no more frequently than once every 10 weeks or no more frequently than once every 12 weeks. The term "once" per month or per 6, 8, 10 or 12 weeks includes not only one single administration (e.g. injection), but also multiple injections into an administration site at one given point in time.

The term "botulinum neurotoxin", in the context of the present invention, is used interchangeably with the term "botulinum toxin". These terms relate to a botulinum toxin which is either a protein free of proteins complexing it, also known as the botulinum toxin "neurotoxic component" or "highly purified" botulinum toxin. The term "botulinum toxin", as used herein, also relates to a protein complex, said protein complex e.g. comprising haemagglutinin (HA protein) combined with botulinum toxin.

The term "botulinum (neuro)toxin", within the present invention, includes botulinum toxins of different types, such as types A, A1, A2, A3, A4, B, C, C1, D, E, F or G.

The term "botulinum toxin", within the present invention, further refers to any molecule possessing or retaining the biological activity of the botulinum toxin, such as a fusion (or chimeric) protein, truncated protein, protein fragment, or a mutated variant of botulinum toxin such as a protein having one or more amino acids added, deleted or replaced.

The term "fusion protein", in the context of the present invention, refers to a botulinum toxin or fragment or mutated variant thereof, obtained after fusion to, or combination with, another molecule, such as e.g. a lipid, glycolipid, peptide, polypeptide, protein, glycoprotein, carbohydrate, polysaccharide, nucleic acid, polyethylene glycol, etc. Such fragments, mutated variants or fused proteins retain the biological activity of botulinum toxin.

The biological activity of botulinum toxin relates e.g. to inhibition of neurotransmission over the synapse at the neuromuscular junction, leading to muscle paralysis or inhibition of exocytosis, in particular exocytosis of acetylcholine or of another neurotransmitter.

The biological activity of botulinum neurotoxin is linked to its proteolytic activity. The botulinum neurotoxins have been shown to possess highly specific zinc-endopeptidase activities within their light sub-units. Depending on the neurotoxin type, these cleave small proteins within the nerve, which are involved in neurotransmitter release. Botulinum toxin types A and E toxins cleave protein SNAP-25. Botulinum toxin types B, D, F and G cleave vesicle-associated membrane protein (VAMP, called synaptobrevin). Botulinum toxin type C cleaves the protein syntaxin. One way to determine the biological activity of any botulinum toxin is therefore to measure the proteolytic activity on the relevant substrate mentioned above. Assays that can be used to determine this activity are known in the art and one such assay is e.g. described in WO 95/33850.

A botulinum toxin to be used in the context of the present invention can e.g. be native, i.e. produced by, extracted and purified from clostridial bacteria (e.g. *Clostridium botulinum*). The botulinum toxin can also be a recombinant protein produced in any other type of host such as other prokaryotic cells, eukaryotic cells, tissues or organisms.

Preferably, the botulinum neurotoxin used according to the invention is chosen from botulinum neurotoxins of types A, A1, A2, A3, A4-A, A4-B, types B, C, C1, D, E, F or G.

The different botulinum neurotoxins types A, A1, A2, A3, A4-A, A4-8 are e.g. described in Jacobson et al., Applied and Environmental Microbiology 2008, Vol. 74(9), p. 2778-2786.

Botulinum neurotoxin type A1 corresponds to the botulinum toxin which is commonly called botulinum toxin type A, without further distinction of subtype.

According to the invention, the botulinum neurotoxin of type A1 can either be a complex of botulinum toxin A1 and haemagglutinin, or to botulinum toxin type A1 free of all complexing proteins (the neurotoxic component of botulinum toxin).

Botulinum neurotoxin type A1 complex is marketed e.g. under the trade names of DYSPORT® or BOTOX®. Botulinum neurotoxin type A1 free from complexing proteins is marketed e.g. under the trade name Xeomin®.

Another botulinum neurotoxin that can be used in the context of the present invention is botulinum toxin type B, marketed under the trade name Myobloc®.

Preferably, the botulinum neurotoxin used in accordance with the present invention is botulinum toxin type A1.

Botulinum toxin type A2 was first isolated from cases of children suffering from botulism around 1990 (Sakaguchi et al., *Int. J. Food Microbiol*. (1990), 11, 231-242).

The botulinum toxin type A2 can be isolated from the following strains: Kyoto-F, Chiba-H, Y-8036, 7103-H, 7105-H, KZ1828, NCTC2012 or NCTC9837 (Cordoba et al., *System. Appl. Microbiol*. (1995), 18, 13-22; Franciosa et al., abstract presented at 40$^{th}$ Interagency Botulism Research Coordinating Committee (IBRCC) Meeting, November 2003).

According to an embodiment of the invention, the botulinum neurotoxin used according to the invention is the botulinum toxin type A2 isolated from the strain *Clostridium botulinum* referenced and accessible under the number NCTC9837, at the National Collection of Type Cultures—Central Public Health Laboratory—London—UK. The strain NCTC9837 is sometimes called the Mauritius 1955 strain.

The botulinum toxin type A2 differs from the toxin A1 by, inter ails, its amino acid sequence, its molecular weight, its immunological and genetic characteristics (Kubota at al., *Biochem, Biophys. Res. Commun*. (1996), 224 (3), 843-848).

In an embodiment, the botulinum neurotoxin used according to the invention can be a fusion protein combined with at least one saccharide or a polysaccharide or a mixture of several polysaccharides.

By polysaccharide is meant within the meaning of the present invention polymers formed by a certain number of monosaccharides having the general formula: —$[C_x(H_2O)_y]_n$— (where y is generally x−1)

Two categories of polysaccharides are distinguished:
homopolysaccharides constituted by the same monosaccharide;
heteropolysaccharides formed by different monosaccharides.

In accordance with the invention, the polysaccharides can be ionic and/or non ionic.

Preferably, the composition comprises at least one polysaccharide predominantly comprising glucose monomer units.

As examples of suitable polysaccharides according to the use of the invention, there can be mentioned starch, starch derivatives, and hydroxyethyl starch in particular 2-hydroxyethyl starch.

The suitable polysaccharides according to the present invention can be substituted, by alkyl radicals, alkoxy radicals, or also by alkyl radicals themselves substituted by alcohol functions.

According to a variant of the invention, the quantity of suitable polysaccharide according to the present invention is at least 1 µg of polysaccharide per 1 unit of botulinum toxin. Depending on the choice of polysaccharide, it is possible to use at least 0.5 µg of polysaccharide per 1 unit of botulinum toxin.

Preferably the botulinum neurotoxin used according to the invention is combined with at least one surfactant or a mixture of several surfactants.

By surfactant is meant within the meaning of the invention an emulsifying agent or a solubilizing agent.

Within the framework of the invention, the surfactants utilized can be chosen from the cationic, anionic or non-ionic surfactants.

Preferably the botulinum neurotoxin used according to the invention is combined with at least one surfactant or a mixture of several surfactants, chosen from the cationic, anionic or non-ionic surfactants.

Preferably the botulinum neurotoxin used according to the invention is combined with at least one surfactant chosen from the non-ionic surfactants of the polysorbates group.

From the polysorbates group, there can be mentioned polysorbate 20, polysorbate 21, polysorbate 40, polysorbate 60, polysorbate 61, polysorbate 65, polysorbate 80, polysorbate 81, polysorbate 85, polysorbate 120, polysorbate 80 acetate.

The preferred surfactant according to a variant of the invention is polysorbate 80.

In accordance with the present invention, the botulinum neurotoxin is preferably administered by injection into one or more sites in an afflicted or painful area of the body. As the inventors of the present invention have surprisingly found that locally administered botulinum toxin has an analgesic effect distant to the site of administration, in accordance with the present invention, administration can also be carried out in a non-afflicted or painless area.

Local administration can e.g. be intramuscular, intradermal, transdermal or sub-cutaneous administration. Administration into the central nervous system (CNS), such as intraspinal or intrathecal administration, is excluded from the present invention.

If the botulinum neurotoxin is to be applied via transdermal administration, preferably a modified botulinum toxin can be used, which is a single, straight-chain, peptide which has two distinct types of domains. The core of the peptide is a sequence of consecutive lysines, each of which confers a positive charge to the peptide. The purpose of this positively charged domain is to form a non-covalent bond with the negatively charged surface of the protein to be transported. The second type of domain is a Protein Transduction Domain (PTD) which is responsible for transcutaneous flux. There are two identical PTDs at each end of the peptide sequence. These PTDs are derived from residues of the transactivator of transcription (TAT) protein. Such a botulinum toxin fusion molecule for transdermal application is available e.g. from Revance Therapeutics, Inc.

If local administration is by injection, the botulinum neurotoxin can preferably be combined with an agent facilitating the injection, also called an injection vehicle or injection vector.

The dose of botulinum neurotoxin used in accordance with the present invention can vary depending on the administration method, the age and the body weight of the subject or patient to be treated as well as the state of the latter, and will be finally decided by the attending doctor. The term "therapeutically effect amount" relates to such a quantity or amount determined by the attending doctor, which leads to relief of the pain treated in accordance with the present invention, is pharmacologically acceptable and does not lead to any serious side effects.

Preferably, the botulinum neurotoxin used according to the invention is administered at a dose comprised between about 0.01 U and about 1500 U, preferably at a dose comprised between about 0.1 U and about 1000 U, more preferably from about 1 to about 500 U, more particularly at a dose comprised between about 10 and about 100 U, e.g. at about 20, 30, 40, 50, 60, 70, 80, or 90 U, whatever the type of botulinum toxin or whatever its origin. The unit of toxin (U) is defined in the experimental part.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLE 1

Measurement of the quantity of the botulinum neurotoxins used in the following example was carried out by using the $LD_{50}$. The $LD_{50}$ corresponds to the semi-lethal dose of a given substance, i.e. the dose (or quantity) which leads to the death of 50% of the animals tested in a group. One unit of toxin (U) corresponds to the $LD_{50}$ in mice by intraperitoneal route.

In the following example, the effect of botulinum toxin type A is measured in an established model of diabetic neuropathy, the streptozotozin-induced neuropathy model.

Analgesic Effect of Local Administration of Botulinum Toxin Type A in the Streptozotocin-Induced Diabetic Neuropathy Model The activity of Dysport® (botulinum toxin of type A1) was evaluated in vivo on a model of diabetic peripheral neuropathy induced by administration of an antineoplastic agent, namely streptozotocin (STZ) which causes the destruction of the beta cells of the islets of Langerhans in the pancreas where insulin is synthesized.

Male Sprague Dawley rats (Charles River) of approximately 280 g were kept indoors for 6 days under animal house conditions. Four groups were made up of at least nine animals.

The neuropathy was induced by intraperitoneal (IP) injections of 65 mg/kg of STZ on day 0 (D0). The blood sugar level of the rats was measured 2 days after the administration of STZ in order to select the diabetic rats having a blood sugar level >300 mg/dl.

Before the first injection, the rats were numbered and weighed and the nociception was evaluated after a mechanical stimulus of increasing pressure: induction of an initial pressure (210 g/mm$^2$) on the rats two rear paws was carried out using an analgesia meter (manufacturer: Ugo Basile, Varese, Italy) according to the Randall-Selitto (RS) method. These measurements make it possible to define the basal values before the neuropathy develops (D-1). The data are expressed in g/40 corresponding to the direct measurement according to the analgesia meter worksheet, which corresponds to the quotient of the mass actually applied (g) divided by 40, i.e. [g/40].

The reduction of the nociceptive threshold, corresponding to the extent of neuropathy, was observed 14 days after the administration of STZ. The nociceptive threshold of both two hind paws was diminished equally. Before the administration of Dysport®, the rats were weighed, the nociception measured and the animals randomized in order to obtain equivalent reduction of the nociceptive threshold in the STZ groups. Dysport® is injected by subplantar (s.p.) route in the rear paw 3 days, 6 days and 9 days after its administration.

Results

Figure 2:
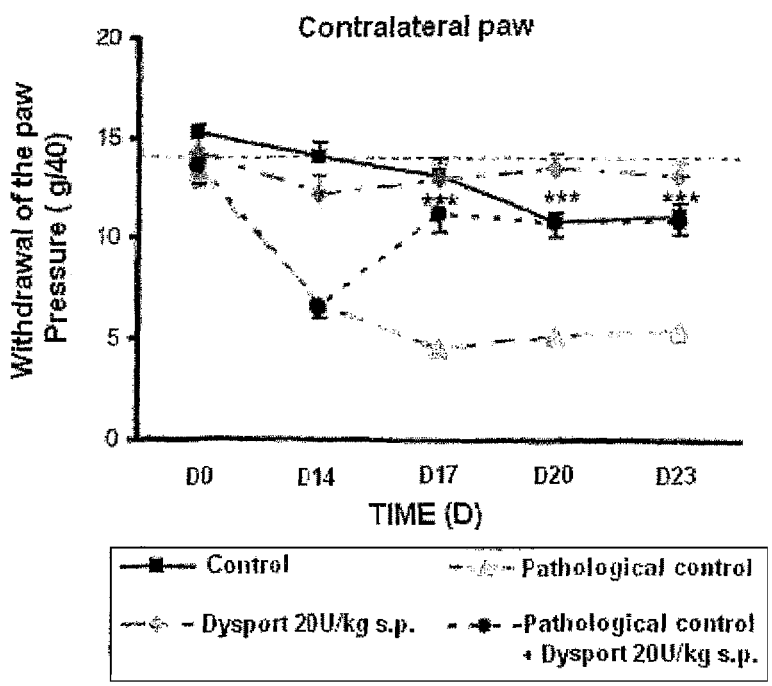
FIG. 2 shows the effect of botulinum toxin type A1 on the left paw (contralateral) following injection by sub-plantar route into the right paw (ipsilateral) in the model of diabetic neuropathy induced by streptozotocin described in Example 1.

The units (g/40) of the ordinate of the graphs shown in FIGS. 1 and 2 measure the weight added to the animal's paw up to the pain threshold which causes a withdrawal movement.

FIG. 1 shows the effect of Dysport® subplantar injection into the right paw in the model of diabetic peripheral neuropathy induced by STZ.

The control indicates the pain threshold tolerated by the rat when an increasing pressure is applied to its paws; the control group was treated with STZ vehicle (0.09 M sodium citrate pH 4.5) by intraperitoneal route and with Dysport® vehicle (0.9% NaCl) by subplantar route.

The pathological control indicates the pain threshold tolerated by the rat when an increasing pressure is applied to its paws after STZ intraperitoneal administration and subplantar Dysport® vehicle administration. The results show that the pressure threshold is lowered in comparison with the control animals, indicating that after i.p. injection of STZ the sensitivity of the rats paws is increased following the application of pressure on them.

The subplantar administration of a 20 U/kg dose of Dysport® in a group treated only with the STZ vehicle by intraperitoneal route, indicates that the pain threshold tolerated by the rat is unchanged. The s.p. administration of a 20 U/kg dose of Dysport® in a group treated with STZ indicates that the pain threshold tolerated by the rat on its right paw increases. The pain threshold following a mechanical stimulus applied to the rats' paws is significantly increased.

FIG. 2 shows the effect of the Dysport® (botulinum toxin of type A) following its injection by subplantar route on the contra-lateral paw (left paw, not injected) in the model of peripheral neuropathy induced by STZ.

The s.p. administration of a 20 U/kg dose of Dysport® in the group treated with STZ increases the pain threshold tolerated by the rat in the contra-lateral paw.

CONCLUSION

The results shown in FIGS. 1, 2 and 3 indicate that the subplantar administration of Dysport® in the right paw of the rats induces an analgesic effect not only in the injected paw but also in the contralateral paw in this model of diabetic neuropathy. This experiment therefore demonstrates an analgesic effect at a site distant to the administration injection site.

The invention claimed is:

1. A method for the treatment of pain associated with diabetic neuropathy comprising local administration of botulinum neurotoxin, wherein the local administration is not in the central nervous system (CNS), and wherein the pain treated is at a site distant from the site of administration.

2. The method of claim 1, wherein said diabetic neuropathy is diabetic neuropathy of an upper limb.

3. The method of claim 1, wherein said diabetic neuropathy is diabetic neuropathy of a lower limb.

4. The method of claim 1, wherein said local administration is into a limb.

5. The method of claim 1, wherein said local administration is into a hand or a foot.

6. The method of claim 5, wherein said local administration is into the palm of a hand or the sole of a foot.

7. The method of claim 1, wherein said local administration is limited to one side of the body.

8. The method of claim 1, wherein said local administration into a site that is distant from a painful site.

9. The method of claim 1, wherein said administration is no more frequent than once per month or nor more frequent than once every six weeks or no more frequently than once every 8 weeks.

10. The method of claim 1, wherein said local administration is sub cutaneous, intra-muscular, intradermal, or transdermal administration.

11. The method of claim 1, wherein the botulinum neurotoxin is selected from botulinum neurotoxin type A, A1, A2, AS, A4, B, C, C1, D, E, F, or G.

12. The method of claim 11, wherein the botulinum neurotoxin is the botulinum toxin of type A1.

13. The method of claim 1, wherein said administration is at a dose between 1 U and 1500 U.

14. The method of claim 13, wherein said administration is at a dose between 100 and 500 U.

* * * * *